(12) United States Patent
Copp et al.

(10) Patent No.: US 8,280,481 B2
(45) Date of Patent: Oct. 2, 2012

(54) ELECTRODES POSSESSING PH INDICATOR

(75) Inventors: Warren Copp, Chicopee, MA (US);
Erick Garstka, Westfield, MA (US);
Christopher Hyatt, South Hadley, MA (US); Kathleen Tremblay, Westfield, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 967 days.

(21) Appl. No.: 12/261,122

(22) Filed: Oct. 30, 2008

(65) Prior Publication Data
US 2009/0270709 A1    Oct. 29, 2009

Related U.S. Application Data

(60) Provisional application No. 60/984,869, filed on Nov. 2, 2007.

(51) Int. Cl.
*A61B 5/04* (2006.01)
*A61N 1/04* (2006.01)
*H01B 1/12* (2006.01)

(52) U.S. Cl. ........ 600/396; 600/395; 600/372; 600/391; 600/392; 607/152; 607/153; 252/519.33

(58) Field of Classification Search .................. 600/382, 600/392, 395, 396; 252/500, 510
See application file for complete search history.

(56) References Cited

U.S. PATENT DOCUMENTS

| | | | | |
|---|---|---|---|---|
| 4,287,153 A | * | 9/1981 | Towsend | 422/412 |
| 4,391,278 A | * | 7/1983 | Cahalan et al. | 600/391 |
| 4,681,576 A | * | 7/1987 | Colon et al. | 604/361 |
| 4,717,378 A | * | 1/1988 | Perrault et al. | 116/201 |
| 4,768,523 A | | 9/1988 | Cahalan et al. | |
| 6,987,133 B2 | | 1/2006 | Chen | |
| 7,036,452 B1 | * | 5/2006 | Tester | 116/207 |
| 2003/0055478 A1 | | 3/2003 | Lyster et al. | |
| 2005/0136077 A1 | | 6/2005 | Yahiaoui et al. | |
| 2005/0137542 A1 | * | 6/2005 | Underhill et al. | 604/361 |
| 2005/0277991 A1 | | 12/2005 | Covey et al. | |
| 2006/0030829 A1 | * | 2/2006 | Flohr et al. | 604/368 |
| 2007/0074590 A1 | * | 4/2007 | Smith | 73/866.1 |
| 2007/0179373 A1 | * | 8/2007 | Pronovost | 600/362 |
| 2007/0282188 A1 | | 12/2007 | Copp-Howland | |
| 2007/0282408 A1 | | 12/2007 | Coggins | |
| 2010/0012018 A1 | * | 1/2010 | Ribi | 116/207 |
| 2010/0112680 A1 | * | 5/2010 | Brockwell et al. | 435/287.9 |
| 2010/0191051 A1 | * | 7/2010 | Miyake et al. | 600/104 |

FOREIGN PATENT DOCUMENTS

EP    0 904 779    3/1999

(Continued)

OTHER PUBLICATIONS

International Search Report from European Application No. EP 10 16 7522 dated Jul. 22, 2010.

(Continued)

*Primary Examiner* — Lee S Cohen
*Assistant Examiner* — Erin M Cardinal
(74) *Attorney, Agent, or Firm* — Lisa E. Winsor

(57) ABSTRACT

The present disclosure provides electrodes that possess components capable of indicating to an end-user when the electrode is in need of replacement. In embodiments, the electrodes include a hydrogel in combination with a pH indicator which changes its color or opacity upon repeated use of the electrode, thereby indicating an appropriate time for changing or replacing the electrode.

16 Claims, 3 Drawing Sheets

FOREIGN PATENT DOCUMENTS

| | | |
|---|---|---|
| EP | 1 133 985 | 9/2001 |
| KR | 2002 0074599 | 10/2002 |
| WO | WO 88/05666 A1 | 8/1988 |
| WO | WO 93/09713 | 5/1993 |
| WO | WO 2005/099606 A1 | 10/2005 |
| WO | WO 2007/142797 A2 | 12/2007 |

OTHER PUBLICATIONS

International Search Report from European Application No. EP 08 25 3592 dated Mar. 6, 2009.

Search Report from corresponding European Application No. EP 10 16 0096 mailed Apr. 4, 2011.

International Search Report from European Application No. EP 10 16 7140 dated Jul. 21, 2010.

Yoshida, K. et al., "Changes in the Skin and Electrode Impedance Spectra Due to Long-Term Surface Stimulation", *Proc. Fifth Annual IFESS Conference*, 2000, 5:282-285.

* cited by examiner

ELECTRODES POSSESSING PH INDICATOR

CROSS-REFERENCE TO RELATED APPLICATIONS

This application claims the benefit of and priority to U.S. Provisional Patent Application No. 60/984,869, filed Nov. 2, 2007, the entire disclosure of which is incorporated by reference herein.

TECHNICAL FIELD

The present disclosure relates to hydrogels suitable for use as conductive compositions, methods of making these compositions, and the use of these compositions with medical electrodes.

BACKGROUND OF RELATED ART

Hydrogels constitute a broad class of materials which may be completely water soluble or swell extensively in water but are not completely water soluble. They have been used in a variety of biomedical applications and may be applied in bulk forms which vary from clear to opaque, and from a relatively stiff to a relatively soft consistency. Sometimes the bulk forms are reinforced by reinforcement members which may be woven or non-woven fabrics to increase the composite strength and/or dimensional stability. Hydrogels have also been used as coatings for various biomedical applications.

Medical electrodes are used to transmit electrical signals or currents between the body of a patient and external medical equipment. These electrodes may include a conductive composition adhered to or otherwise in contact with, the skin of the patient, and a conductor, which is electrically connected to the conductive composition and to the external medical equipment.

Hydrogels for use as conductive compositions with medical electrodes remain desirable.

SUMMARY

The present disclosure provides electrodes that possess components capable of indicating to an end-user when the electrode is in need of replacement. In embodiments, an electrode of the present disclosure may include a substrate, and a conductive composition on at least a portion of a surface of the substrate, the conductive composition including at least one hydrogel and at least one pH indicator component which will change its color or opacity on exposure to a change in pH, thereby providing an indication to replace the electrode.

In other embodiments, an electrode of the present disclosure may include a substrate, and a conductive composition on at least a portion of a surface of the substrate, the conductive composition including at least one hydrogel and at least one pH indicator component that will change its color or opacity on exposure to a specified pH, in some embodiments of from about 2 to about 4, in other embodiments from about 8 to about 10, thereby providing an indication to replace the electrode.

Methods for producing electrodes and the components thereof are also provided, as are methods for their use.

DETAILED DESCRIPTION

Figure 1:
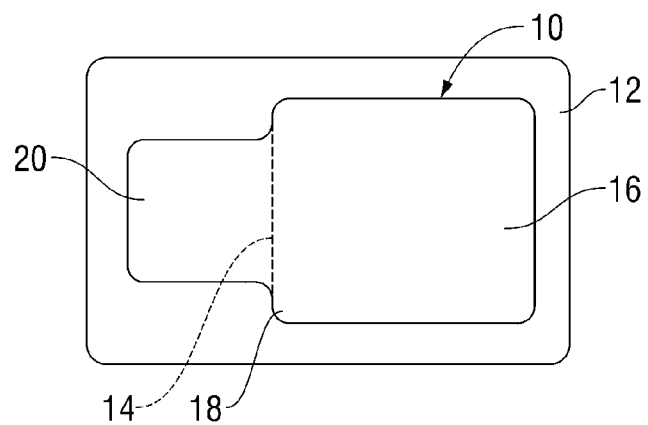
FIG. 1 is a top plan view of a medical electrode including the conductive composition of the present disclosure.

Any adhesive application, including those involving tissue, are within the purview of the hydrogel compositions of the present disclosure. In embodiments, hydrogels may be utilized as adhesives and/or conductive compositions for medical electrodes. The hydrogels of the present disclosure may include components that provide an indication to an end-user that the hydrogel is reaching the end of its useful life and, thus, the electrode should be replaced.

As used herein, the term "hydrogel" may refer to a wide variety of polymer-based compositions. These materials may be synthesized for example from monomer(s) or from monomer(s) mixed with polymer(s) or cross-linked polymer solutions in water. They may be obtained by chemical modification of existing polymer(s) or by adding water to existing dry polymers.

Any biocompatible hydrogel may be utilized in accordance with the present disclosure. Generally speaking, a hydrogel according to the present disclosure may include a coherent, three-dimensional aqueous polymer system capable of imbibing water without liquefying. In embodiments, insolubility in water may be provided by crosslinking the hydrogel polymer. In embodiments, hydrogels or water-containing gels of the present disclosure may include water and various chemical substances including gelatin; polysaccharides; crosslinked acrylamide polymers, hydroxyethylmethacrylate polymers; crosslinked polyhydroxyethylacrylate; polymerized, crosslinked 2-acrylamido-2-methylpropane sulfonic acid polymers or one of their salts such as the sodium or potassium type; crosslinked polyvinylpyrrolidone; polyacrylic acid; copolymers of the aforementioned monomers with each other, copolymers of the aforementioned monomers with other polymers such as polystyrene or other non-hydrogel-forming polymers, one or more salts of the foregoing, and combinations thereof.

For example, by cross-linking homopolymers of an acrylamide derivative such as 2-acrylamido-2-methylpropane-sulfonic acid or one of its salts, hydrogels may be formed. Copolymers thereof may also be formed in the same way with acrylamide. Cross-linked homopolymers of acrylic acid and of methacrylic acid, their salts and copolymers thereof do likewise, as do other acrylic cross-linked homopolymers and copolymers.

Hydrogels of the present disclosure derive their adhesive properties in part from their ability to absorb water. When a relatively dry body of hydrogel contacts moisture, such as the moisture in tissue, particularly internal tissue, or any other moist surface, it develops an aggressive adhesive nature. When the polymer of the hydrogel is crosslinked to an adequate degree, the bulk hydrogel is strong enough, even when swelled with additional liquid, to provide adhesive support for pacing leads, thereby establishing extended connection of the lead to tissue.

Excessive crosslinking decreases the tack of the hydrogel. Too little crosslinking decreases its cohesive strength. Thus, in embodiments, a crosslinking agent may be utilized in forming the polymer suitable as a hydrogel of the present disclosure.

In use, a hydrogel of the present disclosure may contain the polymer or copolymer, and any other additives, including components utilized to form the copolymer, in an amount from about 20% by weight to about 97% by weight of the hydrogel, with the balance being water and/or a humectant.

In some embodiments, a suitable hydrogel for use as a conductive composition may include a copolymer. Non-limiting examples of suitable copolymers may include a first monomer, such as a mixture of acrylic acid and a salt thereof, and a second monomer, such as one of more monomers selected from $CH_2=CHC(O)XR$, in which X is O or NH and R is an unsubstituted or substituted alkyl group of 1 to 5 carbon atoms. The hydrogel may also include water; an electrolyte or mixture of electrolytes; a polymerization initiator; neutralizer a such as sodium hydroxide; optionally, a crosslinking agent; and optionally, a thickener.

In embodiments, a first monomer which may be used to form a copolymer for use in a hydrogel includes acrylic acid, a salt thereof, or a mixture thereof. The copolymer thus produced by polymerization includes acid acrylate moieties ($—CO_2H$ and/or $—CO_2M$, in which M is a cation such as sodium ion, potassium ion, lithium ion, ammonium or substituted ammonium ion, etc.) directly attached to the polymer backbone.

In embodiments, a copolymer utilized in a hydrogel of the present disclosure may include a second monomer which may be one of more monomers selected from $CH_2=CHC(O)XR$, in which X is O or NH and R is an unsubstituted or substituted alkyl group of 1 to 5 carbon atoms. The polymer produced by this polymerization includes groups of the structure $—C(O)XR$ directly attached to the polymer backbone.

Suitable unsubstituted alkyl groups are methyl, ethyl, n-propyl, n-butyl, and n-pentyl. Suitable substituents that may be present in a substituted alkyl group are halo (such as F, Cl, or Br) cyano, carboxylic acid and salts thereof (i.e., $—CO_2H$ or $—CO_2M$, in which M is a cation), phosphate and salts thereof, and sulfonic acid and salts thereof. An example of such a substituted alkyl group is (3-sulfopropyl)acrylic acid ester, potassium salt. Suitable second monomers include 2-acrylamido-2-methylpropane sulfonic acid ($CH_2=CH—CONHC(CH_3)_2—CH_2—SO_3H$) and/or a salt thereof. Suitable salts include the sodium, lithium, potassium, ammonium, and substituted ammonium salts, and mixtures thereof.

In embodiments, the second monomer utilized in a copolymer component of a hydrogel of the present disclosure is 2-acrylamido-2-methylpropane sulfonic acid sodium salt (NaAMPS) ($CH_2=CH—CONHC(CH_3)_2—CH_2—SO_3^-$ $M^+$). Thus, in some embodiments, the first monomer utilized in a copolymer component of a hydrogel of the present disclosure may include a mixture of acrylic acid and sodium acrylate, and the second monomer may include sodium 2-acrylamido-2-methylpropane sulfonate.

The first monomer (acrylic acid and/or salt or salt thereof, calculated as acrylic acid) may be present in an amount of from about 8 wt % to about 85 wt % of copolymer in the hydrogel, in embodiments from about 10 wt % to about 80 wt %, of the total amount of the copolymer in the hydrogel. The second monomer, in embodiments NaAMPS, may be present in an amount of from about 15 wt % to about 92 wt % of the copolymer in the hydrogel, in embodiments from about 20 wt % to about 90 wt % of the copolymer in the hydrogel.

Optionally, an effective amount of a cross-linking agent or mixture of cross-linking agents may be utilized to form the copolymer component of a hydrogel of the present disclosure.

An effective amount of cross-linking agent is an amount that produces a conductive composition with the desired physical properties, such as coherence and adhesion, and electrical properties. Although the amount required will depend on, for example, the molecular weight of the cross-linking agent, the number of ethylenically unsaturated, free radical polymerizable groups present in the cross-linking agent, the amount of free radical polymerizable monomers present in the monomer mix, when the cross-linking agent is present, the amount of crosslinking agent will be present in an amount of from about 0.01 wt % to 1 wt % of the copolymer utilized in the hydrogel, in embodiments from about 0.02 wt % to 0.08 wt % of the copolymer utilized in the hydrogel.

Suitable cross-linking agents include free radical polymerizable monomers that possess more than one ethylenically unsaturated, free radical polymerizable group. Numerous crosslinking agents polymerizable by free-radical initiated polymerization are within the purview of those skilled in the art. Crosslinking agents include, for example, bis-acrylamides and methacrylamides, such as N,N'-methylene bis-acrylamide; acrylate and methacrylate esters of polyols, such as, ethylene glycol diacrylate and dimethacrylate, diethylene glycol diacrylate and dimethacrylate, trimethylolpropane triacrylate and trimethacrylate, ethoxylated trimethylolpropane triacrylate and trimethacrylate; pentaerythritol triacrylate and trimethacrylate, pentaerythritol tetraacrylate and tetramethacrylate, and polyethylene glycol diacrylates and dimethacrylates, such as the diacrylates and dimethacrylates of polyethylene glycols having a molecular weight of from about 200 to about 600. In embodiments, a suitable crosslinking agent may include N,N'-methylene bis-acrylamide [$(CH_2=CHCONH)_2CH_2$].

In embodiments, a polymerization initiator may be utilized with the first monomer and second monomer to form a copolymer for use in a hydrogel of the present disclosure. An effective amount of a polymerization initiator may be combined with the monomers to form such a copolymer. As used herein, an effective amount is an amount that produces efficient polymerization of the monomers under polymerization conditions to produce a hydrogel suitable for use as a conductive composition. Numerous free radical polymerization initiators are within the purview of those skilled in the art. The polymerization initiator may be a single compound or a mixture of compounds. Thermal and/or photo free radical polymerization initiators, for example, may be used.

Suitable thermal free radical polymerization initiators include azo compounds, such as 2,2-azobisisobutyronitrile (AIBN). Suitable photo free radical polymerization initiators are disclosed in "Photoinitiators for Free-Radical-Initiated Photoimaging Systems," by B. M. Monroe and G. C. Weed, *Chem. Rev.*, 93, 435-448 (1993) and in "Free Radical Polymerization" by K. K. Dietliker, in *Chemistry and Technology of UV and EB Formulation for Coatings Inks, and Paints*, P. K. T. Oldring, ed., SITA Technology Ltd., London, 1991, Vol. 3, pp. 59-525. Suitable free radical photo polymerization initiators include, for example, 1-hydroxycyclohexylphenyl ketone (HCPK, IRGACURE® 184); 2-hydroxy-2-methyl-1-phenylpropan-1-one (DAROCUR® 1173); 2-hydroxy-1-[4-(2-hydroxyethoxy)phenyl]-2-methyl-1-propan-1-one (IRGACURE®2959), 2,2-dimethoxy-2-phenylacetophenone (benzildimethyl ketal, BDK, IRGACURE®651), benzophenone, a mixture of 50 wt % benzophenone and 50 wt % of 1-hydroxycyclohexylphenyl ketone (IRGACURE® 500), and combinations thereof.

The polymerization initiator may be present in a copolymer utilized in a hydrogel in an amount less than about 1 wt % of the copolymer, in embodiments less than about 0.7 wt % of the copolymer, in other embodiments less than about 0.4 wt % of the copolymer.

The hydrogel of the present disclosure may also include an electrolyte or a mixture of electrolytes. The electrolyte may be a salt, such as lithium chloride, sodium chloride, potassium chloride, magnesium acetate, ammonium acetate, or a mixture thereof. In embodiments, a suitable electrolyte may include potassium chloride. The hydrogel may possess the electrolyte in an amount from about 0.5 wt % to about 10 wt % of the hydrogel, in embodiments from about 1 wt % to about 8 wt % of the hydrogel.

The hydrogel utilized as a conductive composition may also include a neutralizer. Bases such as hydroxides, amines, Lewis bases, and mixtures thereof may be used as neutralizers. Non-limiting examples of neutralizers include ammonium hydroxide, sodium hydroxide, potassium hydroxide, lithium hydroxide, combinations thereof, and the like. If the acrylic acid and/or the second monomer, such as the 2-acrylamido-2-methylpropane sulfonic acid, are included as monomers in forming a copolymer for use in the hydrogel, it may be desirable to add neutralizer to neutralize some of the acid so that the pH of the mixture is from about 3 to about 6.5. Where utilized, a neutralizer may be present in an amount from about 2 wt % to 8 wt % of the hydrogel.

In addition to a free radical initiator, small amounts of free radical polymerization inhibitors may be present with one or more of the monomers, and/or the crosslinking agent, and/or may be added to the mixture to prevent premature polymerization of the reaction mixture. Suitable free radical polymerization inhibitors include, for example, hydroquinone, 4-methoxyphenol, di-t-butyl-p-cresol, pyrogallol, t-butyl catechol, benzoquinone, 4,4'-thio-bis-(3-methyl-6-t-butylphenol), and 2,2'-methylene-bis-(4-methyl-6-t-butylphenol). When present, the amount of the polymerization inhibitor may be from about 0.01 wt % to about 5 wt % of the hydrogel.

In some embodiments a thickener may be added to the hydrogel. Suitable thickeners include rheological modifiers which permit tailoring the viscosity of the hydrogel to permit its use as a conductive composition with a medical electrode. Non-limiting examples of such thickeners include silica, gums including xanthan gum, polymers including polyvinyl pyrrolidone (PVP), polyacrylamides, polyacrylic acid (including those sold under the name CARBOPOL®), salts thereof, combinations thereof, and the like. Where utilized, a thickener may be present in a hydrogel of the present disclosure in an amount from about 0.1 wt % to about 8 wt % of the hydrogel, in embodiments from about 0.5 wt % to about 5 wt % of the hydrogel.

Other conventional ingredients of conductive compositions may be present in the hydrogel. For example, humectants and medicinal agents, including antimicrobials, antiseptics, analgesics, disinfectants, and the like, may be added to a hydrogel.

Water is present in the mixture. The amount of water includes any water present in any of the ingredients and any water added with ingredients that are in water solution, such as the monomers, the crosslinking agent, the neutralizer, etc. In embodiments, humectants may be added to the water phase of a hydrogel utilized as a conductive composition in an electrode of the present disclosure. Humectants which may be used include non-volatile, non-toxic, water soluble or water miscible viscous liquids at room temperature. Suitable humectants include, but are not limited to, polyhydric alcohols such as glycerol, sorbitol, ethylene glycol, propylene glycol, polyethylene glycols (PEG) of varying molecular weights including PEG 300, PEG 400 and PEG 600, polypropylene glycols, combinations thereof, and the like. The humectant may be utilized in combination with water or without water. Where utilized with water, the ratio of water to humectant may be from about 1:10 to about 10:1.

As noted above, in use, a hydrogel of the present disclosure may contain the polymer or copolymer and any other additives described herein in an amount from about 20% by weight to about 97% by weight, with the balance being water and/or a humectant in an amount from about 3% to about 80% by weight of the hydrogel.

An example of a suitable polymer which may be utilized as the hydrogel includes RG-63B, commercially available from Covidien.

The monomers and any additional components described above may be mixed and spread or coated as a layer on a release liner, for example a siliconized release substrate such as silicone coated polyethylene terephthalate film, or other substrate prior to polymerization. Free radical polymerization may be initiated by, for example, heating the mixture when a thermal free radical polymerization initiator is present in the mixture, or exposing the mixture to actinic radiation when a photoinitiated free radical polymerization initiator is present in the mixture. Any convenient source or sources of actinic radiation providing wavelengths in the region of the spectrum that overlap the absorption bands of the photoinitiated free radical polymerization initiator can be used to activate polymerization. The radiation can be natural or artificial, monochromatic or polychromatic, incoherent or coherent, and for high efficiency should correspond closely in wavelengths to the absorption bands of the polymerization initiator. Conventional light sources include fluorescent lamps, mercury vapor lamps, metal additive lamps, and arc lamps. Useful lasers are those whose emissions fall within or overlap the absorption bands of the photoinitiated free radical polymerization initiator. Although, if desired, the mixture may be degassed before polymerization and/or the polymerization may be carried out under an inert atmosphere, it is not necessary to degas the mixture before polymerization or to carry out the polymerization under an inert atmosphere.

Following polymerization, the resulting conductive composition may transferred to a conductive substrate. Alternatively, the conductive composition may be adhered to a conductive substrate, and the release liner left in place to protect the conductive composition until it is ready for use.

Change Indicating Component

In accordance with the present disclosure, an electrode of the present disclosure also possesses a component which may be utilized to indicate the useful life of the hydrogel has expired or is about to expire. This indication will identify for an end-user that the electrode in use should be replaced and a new electrode should be utilized. In some embodiments, the component indicating that it is time to change the electrode may be included in the hydrogel described above as part of a conductive composition. In other embodiments, the component indicating that it is time to change the electrode may be a separate component applied to an electrode that is not included in the hydrogel described above.

In embodiments, a pH indicator may be added to the hydrogel or utilized separately to indicate it is time to change or replace the electrode. The pH indicator component may change its color or opacity on exposure to a change in pH, thereby providing an indication to replace the electrode. For example, in some embodiments, as the electrode is utilized, hydrolysis of the hydrogel occurs. Hydrolysis of water in the hydrogel may increase the concentration of hydrogen ions in the hydrogel on the anode side, thereby reducing the pH of the hydrogel. The hydroxyl ion increase in concentration on the cathode side will increase the pH of the hydrogel. The pH indicator may be selected so that it develops a color or opacity, or changes color, as the pH drops or increases depending on whether one looks at the anode side or cathode side.

A pH indicator may provide two reasons to indicate the end of the usable life of an electrode: water loss increases the impedance of the electrode, which in turn generates heat, so changing an electrode in response to the pH indicator may avoid thermal burns; and the drop in pH indicates the generation of acid due to hydrolysis, or an increase in pH indicates the production of hydrogel ions, so changing an electrode in response to the pH indicator may avoid chemical burns.

Suitable pH indicators which may be utilized include, but are not limited to, brilliant green, bromophenol blue, m-cresol purple, m-cresol red, eosin Y, methyl orange, methyl violet, combinations thereof, and the like. The pH indicator may be present in a hydrogel in a suitable amount of from about 50 ppm to about 1000 ppm, in embodiments from about 100 ppm to about 900 ppm.

Suitable pH indicators are commercially available from suppliers such as Aldrich Chemicals, Riedel-deHaen, Mallinckrodt Chemicals, Spectrum Chemicals, and the like. Listed below are details regarding some of the above pH indicators, as well as others, which may be utilized in accordance with the present disclosure.

Brilliant green ($C_{27}H_{34}N_2O_4S$), as supplied, is about 90% active crystals, and may be used as about a 1% solution in water. Brilliant green is yellow at a pH of about 0 to about 2.5, and green at a pH of about 2.6 and higher.

Bromophenol blue ($C_{19}H_{10}Br_4O_5$), as supplied, is about 0.04% active solution in water, and the same in use. Bromophenol blue is yellow at a pH of below about 3, and purple at a pH of about 4.6 and above.

m-Cresol purple ($C_{21}H_{18}O_5S$), as supplied, is about 90% active crystals, and may be used as about 0.04% solution in water. m-Cresol purple is yellow at a pH of about 1.2 and lower, and purple at a pH of about 2.8 and higher.

m-Cresol red ($C_{21}H_{18}O_5S$), as supplied, is about 0.04% active solution in water, and the same in use. m-Cresol red is orange at a pH of about 2 and lower, and yellow at a pH of about 3 and higher.

Eosin Y ($C_{20}H_8Br_4O_5$), as supplied, is about 5% active solution in water, and about the same in use. Eosin Y is orange at a pH of about 0, and yellow at a pH of about 3 and higher.

Methyl orange ($C_{14}H_{14}N_3NaO_3S$), as supplied, is about 0.1% active solution in water, and the same in use. Methyl orange is orange at a pH of about 3.1 and below, and yellow at a pH of about 4.4 and higher.

Methyl violet ($C_{24}H_{28}N_3Cl$), as supplied, is about 75% active crystals, and may be used as about 0.02% active solution in water. Methyl violet is yellow at a pH of about 0, and violet at a pH of about 1.6 and higher.

Phenolphthalein ($C_{20}H_{14}O_4$), as supplied, is about 1% active solution in alcohol, and the same in use. Phenolphthalein is colorless at a pH of below about 8, and fuchsia at a pH of above about 8.

Bromocresol green can be utilized at a concentration of about 0.1% in water. Bromocresol green is yellow at a pH of about 3.8 and lower, and blue at a pH of about 5.4 and higher.

Bromocresol green-methyl red is pink at a pH of about 4.6 and lower, and green at a pH of about 5.6 and higher.

Bromocresol purple can be utilized at a concentration of about 0.1% in water. Bromocresol purple is yellow at a pH of about 5.3 and lower, and purple at a pH of about 6.8 and higher.

Bromothymol blue can be utilized at a concentration of about 1% in water. Bromothymol blue is yellow at a pH of about 6 and lower, and blue at a pH of about 7.6 and higher.

Congo red can be utilized at a concentration of about 0.1% in solution. Congo red is blue at a pH of about 3 and lower, and red at a pH of about 5 and higher.

Methyl red can be utilized at a concentration of about 0.1% in water. Methyl red is pink at a pH of about 4.2 and lower, and yellow at a pH of about 6.2 and higher.

Phenol red can be utilized at a concentration of about 0.04% in water. Phenol red is yellow at a pH of about 6.8 and lower, and red at a pH of about 8.2 and higher.

Thymol blue can be utilized at a concentration of about 0.4% in water. Thymol blue is red at a pH of about 1.2 and lower, yellow at a pH of about 2.8 to about 8, and blue at a pH of about 9.2 and higher.

As noted above, in embodiments combinations of pH indicators may be used.

In some embodiments, a pH indicator may be selected which will undergo a change in its appearance, for example change color or develop its color or opacity, at a pH of from about 2 to about 4, in embodiments from about 2.25 to about 3.25. In other embodiments, the dye utilized may develop a color, change color, or become opaque at a pH of from about 8 to about 10, as the electrode is utilized as described above.

In addition, in alternate embodiments, upon changing color or opacity, a message or symbol could become visible indicating it is time to change or replace the electrode. Any symbol that would indicate a time to change the electrode could be utilized. Non-limiting examples of such symbols include "N", "NG", "S", "Stop", "End", "Replace", a skull and cross bones, a frowning face, combinations thereof, and the like.

Medical Electrodes

Medical electrodes transmit electrical signals or currents to or from a patient's skin and an external medical apparatus. Medical electrodes are within the purview of those skilled in the art. These electrodes may include a conductive composition such as a hydrogel of the present disclosure on a substrate. The layer of conductive composition can be adhered to or contacted with the skin of the patient. The medical electrode may also include a conductive interface that is electrically connected to the layer of conductive composition and adapted to be electrically connected to an item of external medical equipment. For many applications, the conductive composition should be sufficiently adhesive to adhere to the patient's skin, i.e., be a conductive adhesive. The configuration of the electrode and the adhesive properties required will depend on the intended application, such as whether the electrode is a transmission electrode, i.e., an electrode that sends electric currents or signals to the patient's body, or a sensing or monitoring electrode, i.e., an electrode that sends electrical signals from the patient's body to external medical equipment.

Figure 2:
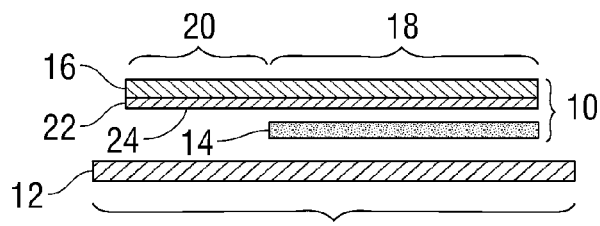
FIG. 2 is a cross-sectional view of the medical electrode of FIG. 1.

FIG. 1 and FIG. 2 show a medical electrode 10 on release liner 12. Release liner 12 is a release paper or film of a waxed or coated plastic, such as a silicone coated polyethylene terephthalate film, which may be used to protect medical electrode 10 before application of the electrode to a skin surface.

Electrode 10 includes a layer of a hydrogel of the present disclosure as conductive composition 14. Electrode 10 also includes conductive interface 16 having a conductor member with a conductive portion 18 contacting layer of conductive composition 14 and tab portion 20 extending beyond layer of conductive composition 14 for mechanical and electrical contact with external medical equipment, such as a electrocardiogram monitoring (ECG) machine, an electroencephalogram (EEG) machine, or a transcutaneous electrical nerve stimulation (TENS) machine (not shown). Conductive interface 16 includes conductive layer 24, coated on at least side 22 of conductive interface 16. Conductive layer 26 contacts layer of conductive composition 14. Medical electrode 10 can be used either as a diagnostic electrocardiogram (ECG or EKG) electrode or as a transcutaneous electrical nerve stimulation (TENS). In use, release liner 12, if present, is removed. The layer of conductive composition 14 of electrode 10 is applied to the surface of the patient's skin and electrically connected to the external medical equipment.

Figure 3:
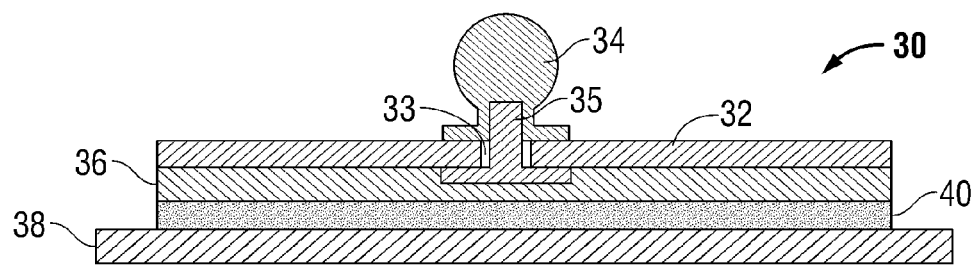
FIG. 3 is a cross-sectional view of a snap medical electrode.

FIG. 3 shows a cross-section of snap medical electrode 30 on a release liner. Electrode 30 has nonconductive backing 32, which has opening 33 covered by snap 34 through which eyelet 35 protrudes. Snap 34 is secured to eyelet 35. Together snap 34 and eyelet 35 provide at least part of a conductive interface adapted to provide an electrical connection between a flexible conductive layer 36 and the external medical equipment (not shown). Eyelet 34 and backing 32 are covered by flexible conductive layer 36 which, in embodiments, may be made of a material such as carbon vinyl. A hydrogel of the present disclosure may be utilized as a conductive composition 40 and adhered to conductive layer 36. Release liner 38 protects the conductive composition 40 prior to use. In embodiments, a complete or partial layer of silver and/or a silver salt such as silver chloride may be placed between conductive composition 40 and conductive layer 36 (not shown), applied as a coating on at least a portion of a surface of conductive layer 124. In embodiments, the electrode may include silver (Ag) or silver/silver-chloride (Ag/AgCl) disposed on at least a portion of the first and/or second sides of the conductive layer.

As noted above, in embodiments an electrode may have a message or symbol that either becomes visible or obscured after use, indicating it is time to replace the electrode. Such a message or symbol, in embodiments, may be placed on the surface of conductive layer 36 adjacent hydrogel 40 (not shown).

In addition, in embodiments, conductive layer 36 and nonconductive layer 32 may possess contiguous windows adjacent each other in each layer (not shown) permitting the visualization of conductive composition 40 during use so that changes in color, opacity, and the like may be observed with an electrode in place on a patient.

In other embodiments, as described above, a heat sensitive component, such as a wax or a thermochromic material, may be applied over eyelet 34 (not shown) or a portion of nonconductive backing 32 adjacent eyelet 34 (not shown). The heat sensitive component may melt, become clear, or change color after repeated use and provide an indication of when an electrode should be changed.

Figure 4:
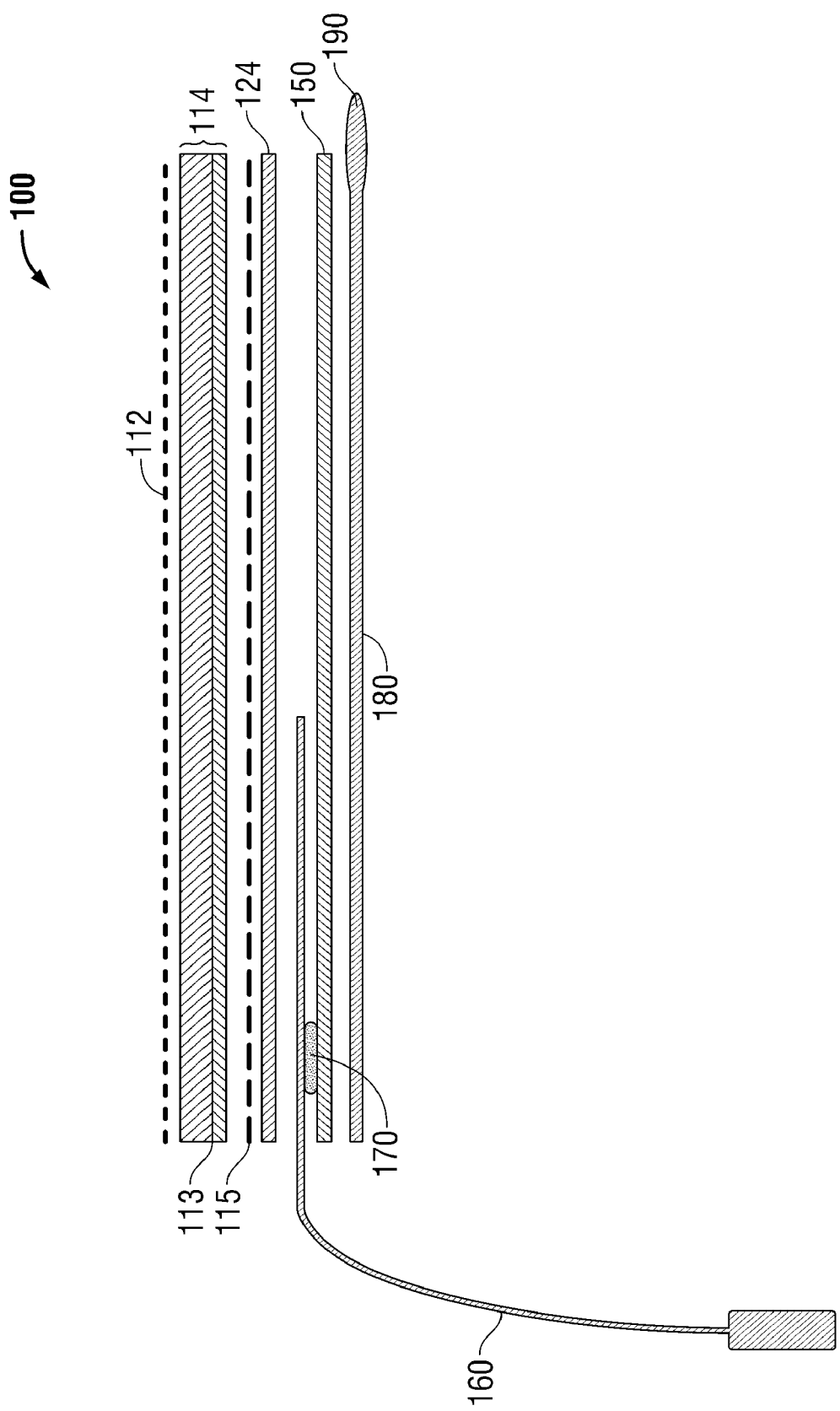
FIG. 4 is a cross-sectional view of an alternate medical electrode of the present disclosure.

FIG. 4 shows a cross-section of an alternate medical electrode 100 on a release liner 112, which may be a polyester film or any other material suitable for use as a release liner. Electrode 100 includes a layer of a hydrogel of the present disclosure possessing a pH indicator as described above as conductive composition 114. In embodiments, conductive composition 114 may have a reinforcement member 113 embedded in the hydrogel, which may be a woven or a nonwoven mesh or any other material, such as a scrim, suitable for forming a reinforcement member. Electrode 100 may also possess a conductive layer 124, which may, in embodiments, be a suitable material such as a conductive carbon film of suitable thickness, in embodiments about 2 mil. In some embodiments, a flood coat or a partial coating of silver ink 115 (which can be a silver and/or silver chloride) may be between conductive layer 124 and conductive composition 114, applied as a coating on at least a portion of a surface of conductive layer 124. In embodiments, the electrode may include silver (Ag) or silver/silver-chloride (Ag/AgCl) disposed on at least a portion of the first and/or second sides of the conductive layer.

Figure 5:
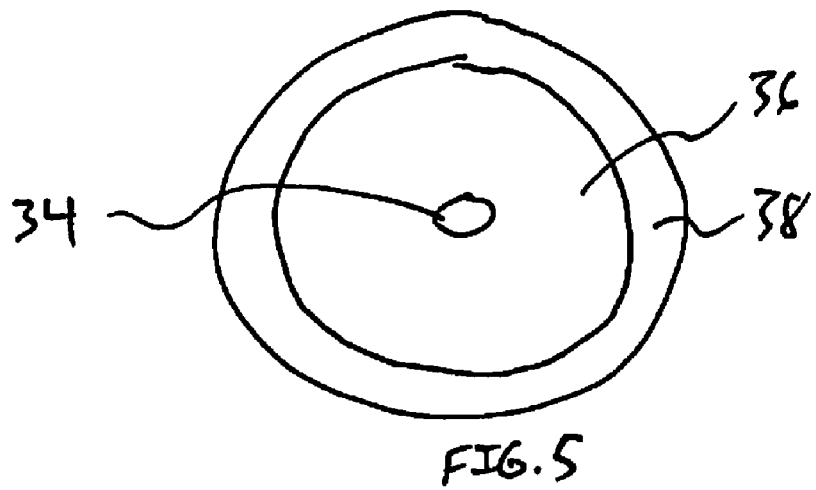
FIG. 5 is a top view of an electrode of the present disclosure prior to use.
Figure 6:
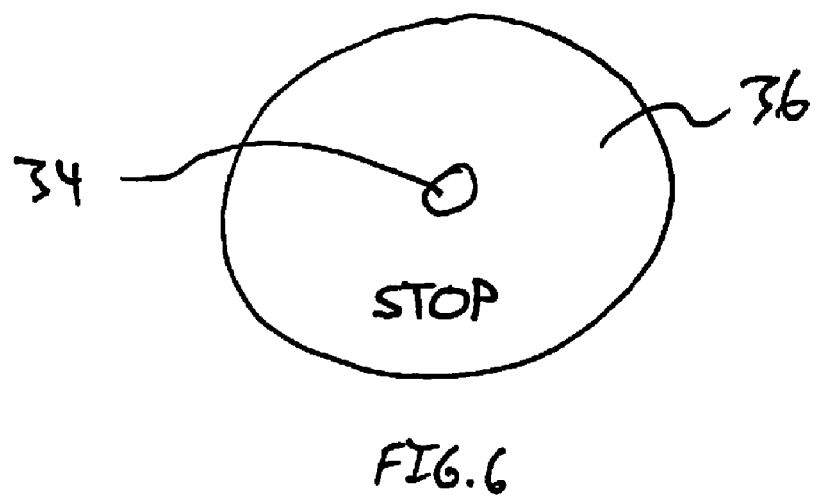
FIG. 6 is a top view of an electrode of the present disclosure after use.

Electrode 100 may also possess a standard stainless steel or tin/copper pig tail lead wire 160 of a suitable length, in embodiments from about 5 to about 15 inches long, in other embodiments about 9 inches long. Lead wire 160 may possess an insulation jacket which, in turn, may be bound to conductive layer 124 using an adhesive 170. Electrode 100 may also possess a reinforcement film 150 having a medical grade pressure sensitive adhesive (PSA) thereon overlying lead wire 160 and affixing reinforcement film 150 to both conductive layer 124 and cover material 180. Finally, cover material 180 may possess pull tab 190 notched out of cover material 180 on the end of electrode 100 opposite the end into which the lead wire 160 enters the electrode. FIG. 5 is a top view of an electrode of the present disclosure prior to use. From the top, flexible conductive layer 36 and overlying release liner 38, are visible. Eyelet 34 is also visible in the center of flexible conductive layer 36. FIG. 6 is a top view of an electrode of the present disclosure after use, and thus does not depict release liner 38. As can be seen in FIG. 6, a message or symbol has become visible on conductive layer 36 after use, in this case the word "STOP", indicating it is time to replace the electrode.

Medical electrodes may be packaged for use in any suitable materials within the purview of those skilled in the art. For example, electrodes may be packaged in materials such as polyethylene or other plastic films, foil barrier packaging, combinations thereof, and the like.

Industrial Applicability

The conductive compositions of the present disclosure may be useful with medical electrodes that can be used with medical equipment for a variety applications, such as: electrocardiogram monitoring (ECG) electrodes (tab and snap style) for monitoring heart activity and for diagnosing heart abnormalities; electroencephalogram (EEG) electrodes; transcutaneous electrical nerve stimulation (TENS) electrodes used for pain management; neuromuscular stimulation (NMS) used for treating conditions such as scoliosis; muscle stimulation electrodes; wound treatment electrodes (accelerated healing of skin wounds or broken bones); defibrillation electrodes to dispense electrical energy to a chest cavity of a mammalian patient to defibrillate heart beats of the patient; iontophoresis; and dispersive electrodes to receive electrical energy dispensed into an incision made during electrosurgery. Other applications of the conductive compositions of the invention include, for example, electro-surgical dispersive pads; drug delivery (passive or iontophoretic); pre-surgical limb or area markers, tapes (anchoring chest tubes, NG tubes, IVs, cannulae, etc); and sterile seals at needle or cannula entry points. The medical equipment used in these applications is within the purview of those skilled in the art.

EXAMPLE 1

A hydrogel sample was prepared containing phenolphthalein as a pH indicator. The purpose was to see if a change in pH of the hydrogel due to hydrolysis was significant enough to be observed over the use duration. About 49.5 grams of RG-63B monomer solution (lot #072686, made Sep. 25, 2007) was combined with about 0.5 grams of a 1% phenolphthalein solution in alcohol.

The monomer solution was first weighed into a clean glass 200 ml beaker. The phenolphthalein solution was added to it and the mix placed under an electric mixer with a prop style blade and mixed for about 5 minutes pulling the vortex half way down the mix shaft. Mixing was stopped and the shaft cleaned. A 25 mil thick film of the monomer was cast on a non-woven polyester scrim on a 5 mil polyester release liner. The film was irradiated for about 30 seconds under a Xenon arc UV lamp. The resulting polymer film was covered with a 2.5-mil polyethylene release liner, pouched and sealed in a poly-foil bag. TENS electrodes were made including this hydrogel. The hydrogel sides of the electrodes were placed on a conductive gel, simulating skin and tissue. They were attached to a commercial TENS device and electrical stimulation was initiated. After about four hours of stimulation, the hydrogel on the cathode side had turned fuchsia, indicating the pH of the hydrogel was 8 or higher.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, or material.

What is claimed is:

1. A medical electrode comprising:
a substrate; and
a conductive composition on at least a portion of a surface of the substrate, the conductive composition comprising at least one hydrogel and at least one pH indicator component which will change its color or opacity on exposure to a change in pH, thereby revealing or obscuring a written message as an indication to replace the electrode.

2. The medical electrode of claim 1, wherein the hydrogel comprises a component selected from the group consisting of gelatin, polysaccharides, crosslinked acrylamide polymers, hydroxyethylmethacrylate polymers, crosslinked polyhydroxyethylacrylate, polymerized, crosslinked 2-acrylamido-2-methylpropane sulfonic acid polymers, crosslinked polyvinylpyrrolidone, polyacrylic acid, copolymers of the foregoing, one or more salts thereof, and combinations thereof, and wherein the hydrogel optionally further comprises an electrolyte present in an amount of from about 0.5% by weight to about 10% by weight of the hydrogel, and optionally further comprises a neutralizer selected from the group consisting of ammonium hydroxide, sodium hydroxide, potassium hydroxide, lithium hydroxide, and combinations thereof.

3. The medical electrode of claim 1, wherein the hydrogel comprises a copolymer comprising a first monomer comprising a mixture of acrylic acid and a salt thereof, present in an amount of from about 8 weight % to about 85 weight % of the hydrogel, and a second monomer of the formula $CH_2=CHC(O)XR$, in which X is O or NH and R is an unsubstituted or substituted alkyl group of from 1 to about 5 carbon atoms present in an amount of from about 15 weight % to about 92 weight % of the hydrogel.

4. The medical electrode of claim 1, wherein the hydrogel further comprises a cross linking agent selected from the group consisting of N-N'-methylene bis-acrylamide, diethylene glycol diacrylate, diethylene glycol dimethacrylate, trimethylolpropane triacrylate, trimethylolpropane trimethacrylate, ethoxylated trimethylolpropane triacrylate, ethoxylated trimethylolpropane trimethacrylate, pentaerythritol triacrylate, pentaerythritol trimethacrylate, pentaerythritol tetraacrylate, pentaerythritol tetramethacrylate, polyethylene glycol diacrylate, polyethylene glycol dimethacrylate, and combinations thereof, optionally a polymerization initiator selected from the group consisting of 2,2-azobisisobutyronitrile, 1-hydroxycyclohexylphenyl ketone, 2-hydroxy-2-methyl-1-phenylpropan-l-one, 2-hydroxy-1[4-(2-hydroxyethoxy)phenyl]-2-methyl-l-propan-l-one, 2,2-dimethoxy-2-phenylacetophenone, benzophenone, and combinations thereof, and wherein the electrode further comprises a conductive layer possessing a coating of silver or silver/silver-chloride on at least a portion of a surface of the conductive layer.

5. The medical electrode of claim 1, wherein the at least one pH indicator is selected from the group consisting of brilliant green, bromophenol blue, m-cresol purple, m-cresol red, eosin Y, methyl orange, methyl violet, phenolphthalein, bromocresol green, bromocresol purple, bromothymol blue, congo red, methyl red, phenol red, thymol blue, and combinations thereof.

6. The medical electrode of claim 1, wherein the at least one pH indicator is present in the hydrogel in an amount of from about 50 ppm to about 1000 ppm.

7. A medical electrode comprising:
a substrate; and
a conductive composition on at least a portion of a surface of the substrate, the conductive composition comprising at least one hydrogel and at least one pH indicator component that will change its color or opacity on exposure to a pH of from about 2 to about 4 thereby revealing or obscuring a written message as an indication to replace the electrode.

8. The medical electrode of claim 7, wherein the hydrogel comprises a component selected from the group consisting of gelatin, polysaccharides, crosslinked acrylamide polymers, hydroxyethylmethacrylate polymers, crosslinked polyhydroxyethylacrylate, polymerized, crosslinked 2-acrylamido-2-methylpropane sulfonic acid polymers, crosslinked polyvinylpyrrolidone, polyacrylic acid, copolymers of the foregoing, one or more salts thereof, and combinations thereof, and wherein the hydrogel optionally further comprises an electrolyte present in an amount of from about 0.5% by weight to about 10% by weight of the hydrogel, and optionally further comprises a neutralizer selected from the group consisting of ammonium hydroxide, sodium hydroxide, potassium hydroxide, lithium hydroxide, and combinations thereof.

9. The medical electrode of claim 7, wherein the hydrogel comprises a copolymer comprising a first monomer comprising a mixture of acrylic acid and a salt thereof, present in an amount of from about 8 weight % to about 85 weight % of the hydrogel, and a second monomer of the formula $CH_2=CHC((O))XR$, in which X is O or NH and R is an unsubstituted or substituted alkyl group of from 1 to about 5 carbon atoms present in an amount of from about 15 weight % to about 92 weight % of the hydrogel.

10. The medical electrode of claim 7, wherein the hydrogel further comprises a cross linking agent selected from the group consisting of N-N'-methylene bis-acrylamide, diethylene glycol diacrylate, diethylene glycol dimethacrylate, trimethylolpropane triacrylate, trimethylolpropane trimethacrylate, ethoxylated trimethylolpropane triacrylate, ethoxylated trimethylolpropane trimethacrylate, pentaerythritol triacrylate, pentaerythritol trimethacrylate, pentaerythritol tetraacrylate, pentaerythritol tetramethacrylate, polyethylene glycol diacrylate, polyethylene glycol dimethacrylate, and combinations thereof, optionally a polymerization initiator selected from the group consisting of 2,2-azobisisobutyronitrile, 1-hydroxycyclohexylphenyl ketone, 2-hydroxy-2-methyl-1-phenylpropan-1-one, 2-hydroxy-1-[4-(2-hydroxyethoxy)phenyl]-2-methyl-1-propan-1-one, 2,2-dimethoxy-2-phenylacetophenone, benzophenone, and combinations thereof, and wherein the electrode further comprises a conductive layer possessing a coating of silver or silver/silver-chloride on at least a portion of a surface of the conductive layer.

11. The medical electrode of claim 7, wherein the at least one pH indicator is selected from the group consisting of brilliant green, bromophenol blue, m-cresol purple, m-cresol red, eosin Y, methyl orange, methyl violet, bromocresol green, congo red, thymol blue, and combinations thereof, present in the hydrogel in an amount of from about 50 ppm to about 1000 ppm.

12. A medical electrode comprising:
a substrate; and
a conductive composition on at least a portion of a surface of the substrate, the conductive composition comprising at least one hydrogel and at least one pH indicator component that will change its color or opacity on exposure to a pH of from about 8 to about 10 thereby revealing or obscuring a written message as an indication to replace the electrode.

13. The medical electrode of claim 12, wherein the hydrogel comprises a component selected from the group consisting of gelatin, polysaccharides, crosslinked acrylamide polymers, hydroxyethylmethacrylate polymers, crosslinked polyhydroxyethylacrylate, polymerized, crosslinked 2-acrylamido-2-methylpropane sulfonic acid polymers, crosslinked polyvinylpyrrolidone, polyacrylic acid, copolymers of the foregoing, one or more salts thereof, and combinations thereof, and wherein the hydrogel optionally further comprises an electrolyte present in an amount of from about 0.5% by weight to about 10% by weight of the hydrogel, and optionally further comprises a neutralizer selected from the group consisting of ammonium hydroxide, sodium hydroxide, potassium hydroxide, lithium hydroxide, and combinations thereof.

14. The medical electrode of claim 12, wherein the hydrogel comprises a copolymer comprising a first monomer comprising a mixture of acrylic acid and a salt thereof, present in an amount of from about 8 weight % to about 85 weight % of the hydrogel, and a second monomer of the formula $CH_2=CHC(O)XR$, in which X is O or NH and R is an unsubstituted or substituted alkyl group of from 1 to about 5 carbon atoms present in an amount of from about 15 weight % to about 92 weight % of the hydrogel.

15. The medical electrode of claim 12, wherein the hydrogel further comprises a cross linking agent selected from the group consisting of N-N'-methylene bis-acrylamide, diethylene glycol diacrylate, diethylene glycol dimethacrylate, trimethylolpropane triacrylate, trimethylolpropane trimethacrylate, ethoxylated trimethylolpropane triacrylate, ethoxylated trimethylolpropane trimethacrylate, pentaerythritol triacrylate, pentaerythritol trimethacrylate, pentaerythritol tetraacrylate, pentaerythritol tetramethacrylate, polyethylene glycol diacrylate, polyethylene glycol dimethacrylate, and combinations thereof, optionally a polymerization initiator selected from the group consisting of 2,2-azobisisobutyronitrile, 1-hydroxycyclohexylphenyl ketone, 2-hydroxy-2-methyl-1-phenylpropan-1-one, 2-hydroxy-1-[4-(2-hydroxyethoxy)phenyl]-2-methyl-1-propan-1-one, 2,2-dimethoxy-2-phenylacetophenone, benzophenone, and combinations thereof, and wherein the electrode further comprises a conductive layer possessing a coating of silver or silver/silver-chloride on at least a portion of a surface of the conductive layer.

16. The medical electrode of claim 12, wherein the at least one pH indicator is selected from the group consisting of phenolphthalein, bromothymol blue, phenol red, thymol blue, and combinations thereof, present in the hydrogel in an amount of from about 50 ppm to about 1000 ppm.

* * * * *